United States Patent [19]
Gowda et al.

[11] Patent Number: 5,808,074
[45] Date of Patent: Sep. 15, 1998

[54] BENZOYLECGONINE CONJUGATE DIAGNOSTIC REAGENTS

[75] Inventors: D. Channe Gowda, Gaithersburg, Md.; Eugene A. Davidson, Washington, D.C.

[73] Assignee: Georgetown University, Washington, D.C.

[21] Appl. No.: 792,227

[22] Filed: Jan. 31, 1997

Related U.S. Application Data

[60] Provisional application No. 60/011,045 Feb. 2, 1996.
[51] Int. Cl.⁶ .................. C07D 451/10; C07D 451/12; G01N 33/53
[52] U.S. Cl. ................ 546/130; 435/7.9; 530/359; 530/363; 530/849; 546/125
[58] Field of Search ................. 546/131, 127, 546/130

[56] References Cited

U.S. PATENT DOCUMENTS

| | | | |
|---|---|---|---|
| 3,817,837 | 6/1974 | Rubenstein et al. | 435/7.9 |
| 3,917,582 | 11/1975 | Soffer et al. | 530/363 |
| 4,123,431 | 10/1978 | Soffer et al. | 546/130 |
| 4,197,237 | 4/1980 | Leute et al. | 530/389.8 |
| 5,066,789 | 11/1991 | Srinivasan et al. | 530/388 |
| 5,233,042 | 8/1993 | Buechler | 546/129 |
| 5,369,007 | 11/1994 | Kidwell | 435/7.9 |
| 5,376,667 | 12/1994 | Somers et al. | 514/304 |

OTHER PUBLICATIONS

Chemical Abstracts,vol.124:(No.19),abst.No.252,834k,May 6, 1996.

*Primary Examiner*—Alan L. Rotman
*Attorney, Agent, or Firm*—Oliff & Berridge, PLC

[57] ABSTRACT

A benzoylecgonine conjugate represented by the following formula:

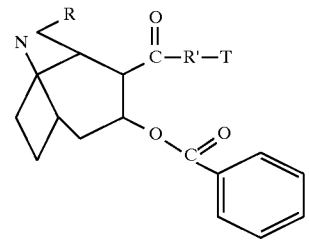

wherein, R is H or $CH_3$; R' is $-NH-NH-$, $-(NH)_2-CO-(CH_2)_n-CO-NH-NH-$, or related linear chains wherein at least one $(CH_2)$ is replaced with a substituent selected from the group consisting of an ether, an amide, a sulfide, a disulfide, an alkyl, an aryl, an alkoxy, an aryloxy or an alkylhalide; and T is a targeting substance selected from the group consisting of proteins, peptides, antigens, polypeptides, dyes, biotins, enzymes, antibodies, hormones, carbohydrates, polysaccharide supports, and filter paper.

4 Claims, 8 Drawing Sheets

CROSS-LINKING OF BENZOYLECGONINE DERIVATIVES TO PROTEINS
SCHEMATIC DIAGRAM

BENZOYLECGONINE —— PROTEIN CONJUGATES

CROSS-LINKING OF BENZOYLECGONINE TO DYE
SCHEMATIC DIAGRAM

BENZOYLECGONINE CONJUGATE DIAGNOSTIC REAGENTS

This nonprovisional application claims the benefit of U.S. Provisional Application No. 60/011,045, filed Feb. 2. 1996.

FIELD OF THE INVENTION

The present invention relates to benzoylecgonine conjugates that are useful as diagnostic reagents for cocaine detection methodology. This invention also relates to methods of synthesizing benzoylecgonine conjugates.

BACKGROUND

A wide variety of ways have been developed for determining minute quantities of various organic compounds. A number of agents have been used for the detection of various organic compounds. These agents are conjugated with receptors, detector molecules, antibodies, antigens, etc. that recognize particular compounds or a class of compounds. The most common type of receptor is an antibody that is able to strongly bind to a particular spatial conformation and polar or non-polar distribution.

In order to prepare antibodies for compounds which are not antigenic, the non-antigenic compound is normally bonded or conjugated to an antigenic material, usually a protein. With most compounds, it is necessary to modify the compound of interest that bonds to the antigen.

In some immunoassays, it is necessary to bond the compound to be detected to a detector molecule (reporter molecule). The link that is chosen for bonding this compound to the antigen or to the detector molecule must allow not only for satisfactory bonding to these molecules, but also must allow an antibody to recognize the compound when it is bound to the detector molecule.

In addition, the linking group must not significantly change the polar characteristics of the compound to be assayed nor detrimentally affect the molecules to which the compound is bonded. Depending on the properties of the particular material to which the compound is to be bonded, the linking group should permit a sufficient number of the desired compounds to be bonded to the antigen, antibody or detector molecule. Additional considerations include synthetic simplicity, chemical stability, the effect of the bonding functionality on the material to which it is bonded, and the particular site on the material, for example a protein, to which the compound will be bonded.

Benzoylecgonine is a key metabolite of cocaine and structurally they are closely related. Monoclonal and polyclonal antibodies raised against benzoylecgonine cross react with cocaine. Benzoylecgonine has a free carboxylic group which can be used as a site for conjugation to various proteins for immunological characterization of cocaine. Benzoylecgonine-horseradish peroxidase conjugate (BE-HRP) can be used as a diagnostic reagent for detection of cocaine employing standard immunological assay procedures.

Generally, primary amine or carboxylic group containing haptens are conjugated to antibodies and enzymes by using water-soluble carbodiimides. The reactions are invariably random and may lead to drastic reductions in antibody and enzyme activity. An alternative and a better approach would be aldehyde-amine condensation utilizing amino groups of haptens and aldehyde groups generated on the carbohydrate moieties of glycoproteins. Since the carbohydrate moieties of antibodies and enzymes are generally not required for their activities, conjugation of haptens through the carbohydrate moieties should not affect their activities. However, in this process condensation of a primary amine to an aldehyde group yields an unstable Schiff base which has to be reduced using sodium cyanoborohydride to obtain stable conjugates. The yields of conjugates are often low because Schiff bases are unstable at the pH employed for the cyanoborohydride reduction. Moreover, the use of cyanoborohydride may lead to a decrease in the biological activity.

U.S. Pat. No. 5,066,789 to Srinivasan et al. describes Schiff base hydrazone linkages for conjugation. A diagnostic or therapeutic agent is converted into an agent-hydrazide through reaction with a maleimidehydrazide heterobifunctional linker. The free aldehyde group of the targeting substance-linker is then reacted with the diagnostic/therapeutic agent-linker hydrazide, yielding a targeting substance conjugate. The targeting substance hydrazide is covalently attached through a stabilized Schiff base linkage to an aldehyde or ketone group present on a diagnostic or therapeutic agent.

U.S. Pat. No. 5,369,007 to Kidwell describes a microassay on a card which is useful for drug testing. The reference also describes the preparation of a cocaine-enzyme conjugate. Aldehyde containing HRP is reacted with p-aminococaine to obtain a p-aminococaine-horseradish peroxidase conjugate.

U.S. Pat. No. 4,197,237 to Leute et al. describes nitrogen derivatives of benzoyl ecgonine and cocaine, particularly amino, diazonium, and diazo derivatives. The enzyme may be conjugated to the nitrogen derivatives of benzoyl ecgonine and cocaine. Various enzymes may be used such as oxidoreductases, oxidases, reductases, etc.

U.S. Pat. No. 4,123,431 to Soffer et al. describes non-oxo-carbonyl substituted derivatives of cocaine which may be conjugated with other compounds for detection of cocaine. Protein molecules (enzymes) may be conjugated with the non-oxo-carboxyl derivatives. Non-ecgonine may displace chlorine on a haloaliphatic carboxylic acid and subsequently be activated using carbodiimide.

U.S. Pat. No. 3,917,582 to Soffer et al. describes benzoyl ecgonine derivatives having an isothiocyanate group for conjugation to polypeptides and proteins for immunoassays. Particularly, the isothiocyanate is conjugated to enzymes or antigenic polypeptides or proteins. The enzyme conjugate is utilized for detection of benzoyl ecgonine. The isothiocyanate compound is prepared by esterifying benzoyl ecgonine followed by hydrogenation and subsequent derivation using thiophosgene. The isothiocyanate is then conjugated to a poly(amino acid). The poly(amino acid) may be an oxidase.

U.S. Pat. No. 5,233,042 to Buechler describes derivatives of cocaine which are conjugated to antigenic proteins or polypeptides for use in immunoassays. The preferred derivatives are the ethyl amide benzoyl ecgonine derivatives. Benzoyl ecgonine hydrate is added to an amide benzoic acid and carboxyldiimidazole, the product of which is then reacted with ethyl amine hydrochloride.

U.S. Pat. No. 5,376,667 to Somers et al. describes benzoyl ecgonine, ecgonine and ecgonidine derivatives which are utilized in pharmaceutical compositions. The products are obtained by reacting propylene glycol with cocaine.

U.S. Pat. No. 3,817,837 to Rubenstein et al. describes enzyme-ligand conjugates and various linking groups between the conjugate of ligand-enzyme. The ligand-enzyme conjugate may be used to detect narcotics. The ligands may be narcotics, such as morphine. The enzymes may be peroxidases.

SUMMARY OF THE INVENTION

The present invention relates to the application of conjugates of benzoylecgonine. The invention also relates to methods of synthesizing benzoylecgonine conjugates using hydrazide derivatives of benzoylecgonine.

Hydrazide derivatives of benzoylecgonine are prepared by carbodiimide-activated coupling of benzoylecgonine to hydrazide derivatives. The benzoylecgonine hydrazide derivatives are then coupled to the carbohydrates, polypeptides, proteins (enzymes, antibody, glycoproteins), polysaccharides, filter paper supports, related carbohydrates, dyes, biotins or the like.

The benzoylecgonine conjugates may be used, for example, in screening anticocaine antibodies, detection of cocaine, cocaine receptor studies and in immunoassay processes. Cocaine receptor studies.

DESCRIPTION OF PREFERRED EMBODIMENTS

Figure 1:
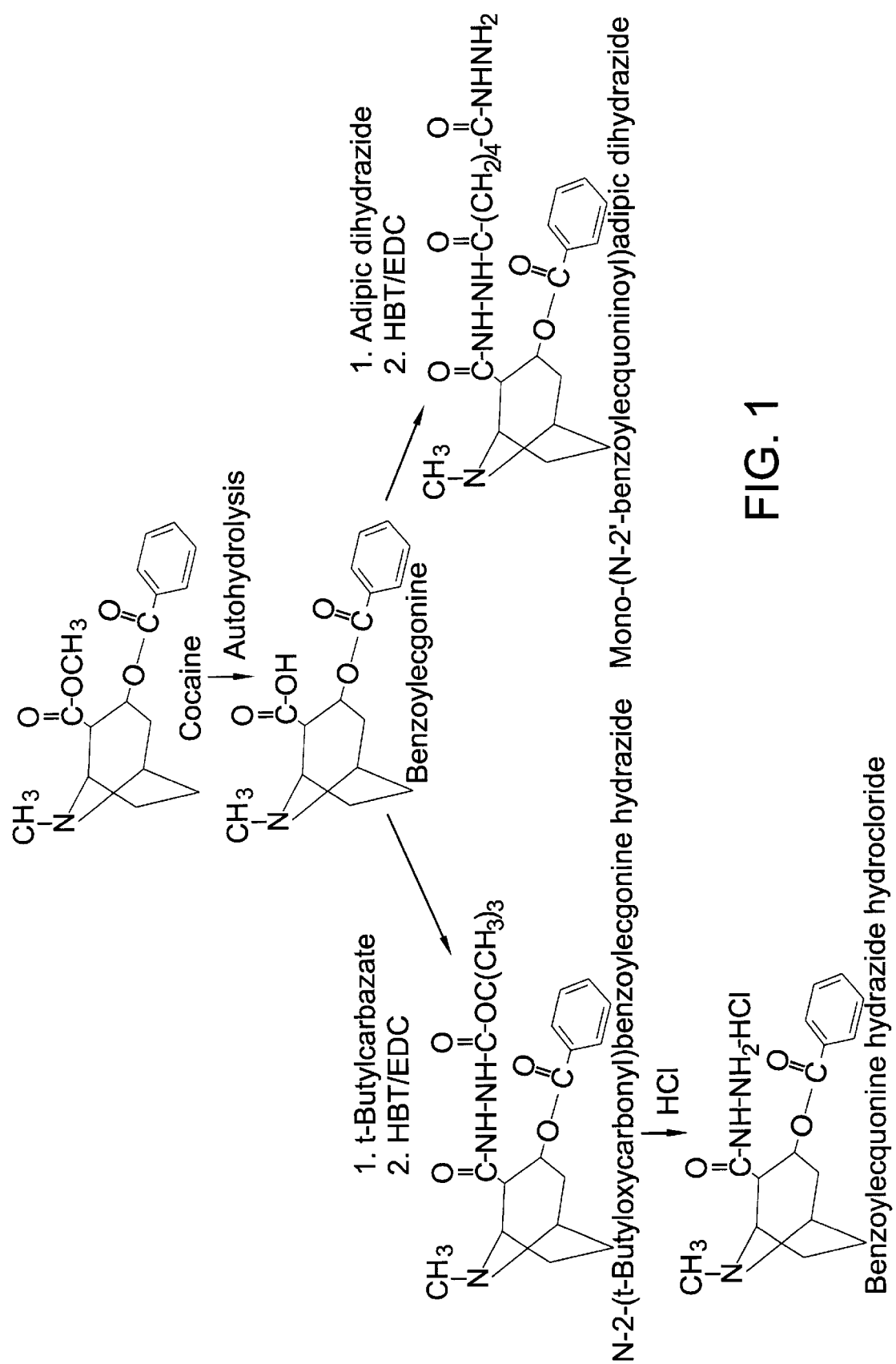
FIG. 1 illustrates a scheme for the synthesis of benzoylecgonine hydrazide and mono-N-(2'-benzoylecgoninoyl)adipic dihydrazide.

Benzoylecgonine conjugates can be used as a diagnostic reagent in immunoassays for the detection of cocaine, for example in illicit drug samples and cocaine and its metabolites in biological fluids. This invention relates to the preparation and characterization of benzoylecgonine conjugates.

The compounds of the present invention are derivatives of cocaine and cocaine metabolites, primarily derivatives of benzoylecgonine. The carboxyl group of benzoylecgonine is modified with hydrazide derivatives to provide a site for attachment to proteins, glycoproteins, polypeptides, carbohydrates, filter paper, polyaccharides, dyes, biotins or the like. The synthesis of the benzoylecgonine conjugates are designed such that they are displaced from the bound proteins, polypeptides, polysaccharide supports, filter papers, or the like, by cocaine or its metabolites.

In general, the benzoylecgonine derivatives of this invention have the following formula:

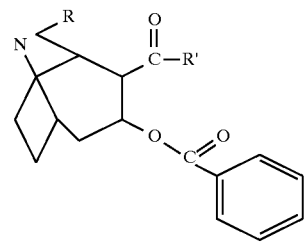

wherein:
R is H or $CH_3$; or
R' is $-NH-NH_2$, $(NH)_2CO(CH_2)_nCONHNH_2$, or related linear chains containing hydrazide functional groups; and
n is an integer of 0 to 20, preferably 1 to 10, and more preferably 1 to 5.

According to the present invention, a targeting substance is a moiety that binds to a defined population of cells. For example, "targeting substance" includes targeting or labeled proteins, peptides, biotins, or the like, capable of binding receptors, enzymatic substances, antigenic determinants, antibodies, or other binding sites present on a target cell population. As used herein, "targeting substance" also includes non-proteinaceous moieties such as dyes.

A conjugate is a hybrid molecule wherein the components are joined by one or more covalent chemical linkages. A conjugate may include, for example, a targeting substance, peptide or protein antigens, detector molecules (enzymes, dyes, antibodies, biotins or the like), or an antibody (i.e., an immunoconjugate).

Conjugates according to the present invention are prepared from the above benzoylecgonine derivatives. The conjugates have the following formula:

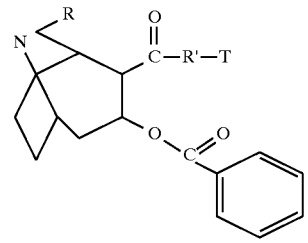

wherein:
R is as above.
R' is —NH—NH or $-(NH)-_2CO-(CH_2)-NH-NH-$; and
T is a targeting substance comprising proteins, peptides, polypeptides, dyes, biotins, enzymes, antibodies, carbohydrates, polysaccharide supports, filter paper, etc., or the like.

Polypeptides of the present invention may encompass from about 2 to 1000 amino acid units (usually less than about 120,000 molecular weight). Larger polypeptides are usually called proteins. Some proteins are usually composed of 1 to 20 polypeptide chains, called subunits, which are bound by covalent or non-covalent bonds. Subunits are normally of from 100 to 300 amino acid groups (approximately 10,000 to 35,000 molecular weight). For the purposes of this invention, poly(amino acid) is intended to include individual polypeptide units, or polypeptides which are subunits of proteins, whether composed solely of polypeptide units or polypeptide units in combination with other functional groups, such as porphyrins, as in hemoglobin or cytochrome oxidase.

Various protein types may be employed as the targeting substance, detectors molecule, antigens, etc. These types include albumin, serum proteins, e.g., globulins, ocular lens proteins, lipoproteins, etc. Illustrative proteins include bovine serum albumin, keyhole limpet hemocyanin, egg ovalbumin, bovine γ-globulin, etc. Small natural polypeptides which are immunogenic, such as gramicidin may also be employed. Various synthetic poly(amino acids) may also be employed, such as polymers of lysine, glutamic acid, phenylalanine, tryosine, etc., either by themselves or in combination. Of particular interest is polylysine or a combination of lysine and glutamic acid. Any synthetic polypeptide must contain a sufficient number of active groups, as for example, amino groups provided by lysine.

Various enzymes may be used as the targeting substance, reporter or detector molecules, such as oxidoreductases, hydrolases, lyases, and the like. These enzymes include esterases, amidases, phosphorylases, carbohydrases, peroxidases, oxidases, reductases and the like. Of particular interest are such enzymes as lysozyme, amylase, dehydrogenases, such as malate deydrogenase, lactate dehydrogenase, mannitol-1-phosphate dehydrogenase, and glucose 6-phosphate dehydrogenase, β-glucuronidase, cellulase, and phospho-lipase, particularly horseradish peroxidase. The enzymes will usually have molecular weights in the range of about $1 \times 10^4$ to $6 \times 10^5$, more usually in the range of about $1.2 \times 10^4$ to $3 \times 10^5$.

Targeting or detector substances useful within the present invention also include antibody and antibody fragments; peptides, such as bombesin, gastrin-releasing peptide, RGD peptide, substance P, neuromedin-B, neuromedin-C, and metenkephalin; and hormones, such as EGF, α- and β-TGF, estradiol, neurotensin, melanocyte stimulating hormone, follicle stimulating hormone, luteinizing hormone, and human growth hormone. Biotin, avidin, proteins corresponding to known cell surface receptors (including low density lipoproteins, transferrin, insulin and $CD_4$), fibrinolytic enzymes, and biological response modifiers (including interleukin, interferon, erythropoietin and colony-stimulating factor) are also suitable targeting substances. Analogs of the above listed targeting substances that retain the capacity to bind to a defined target cell population may also be used within the claimed invention. In addition, synthetic targeting substances may be designed by peptide synthetic or recombinant DNA techniques.

According to the present invention, convenient methods have been developed for the covalent attachment of benzoylecgonine to targeting substances (e.g., proteins, polypeptides, dyes, biotins, enzymes, antibodies, carbohydrates, polysaccharides, filter paper, etc.) through its oligosaccharide chains.

For example, to take advantage of the facile aldehyde-hydrazide condensation reactions at acidic pH to form hydrazones, hydrazide derivatives of benzoylecgonine are synthesized. The hydrazides are purified, characterized and then coupled to targeting substances or detector molecules (e.g., proteins, polypeptides, dyes, biotins, etc.) through appropriate functional groups and to glycoprotein through carbohydrate residues in a site specific manner.

As another example, in a more simplistic approach, the terminal sugar residues in targeting substances or detector molecules (e.g., proteins, glycoproteins, enzymes, antibodies) are derivatized with adipic dihydrazide. A large molar excess of the adipic dihydrazide may be used to ensure that only one end condenses with the aldehyde groups on the carbohydrate moieties of the targeting substance. The hydrazide-derivatized targeting substance is then reacted with the carbodiimide-activated benzoylecgonine under acidic conditions to ensure that the hydrazide moieties rather than amino groups of the polypeptide chain of the targeting substance react with benzoylecgonine. Therefore, it is believed that this approach also gives carbohydrate site-directed coupling.

The presence of covalently bound benzoylecgonine in the benzoylecgonine conjugates may be demonstrated, for example, by dot blot analysis using anti-benzoylecgonine antibodies. The stoichiometry of benzoylecgonine to the targeting substance may be determined reliably by MALDI-MS analysis.

The procedures described herein provide convenient approaches for the preparation of benzoylecgonine conjugates. Approximately 4 to 10 benzoylecgonine residues could be coupled to one mole of the targeting substance by using two of the benzoylecgonine hydrazides described herein. Further, it is possible to obtain benzoylecgonine conjugates containing the desired amounts of benzoylecgonine (in the range of 1 to 10 moles per mole of the targeting substance) by controlling the degree of periodate oxidation and thus the number of sugar residues oxidized.

For example, hydrazide derivatives of benzoylecgonine, e.g., N-2-(t-butyloxycarbonyl) benzoylecgonine hydrazide and mono-(N-2'-benzoylecgoninoyl)adipic dihydrazide, may be synthesized by carbodiimide-activated coupling of benzoylecgonine to N-2-(t-butyloxycarbonyl) hydrazide and adipic dihydrazide, respectively. Removal of the t-butyloxycarbonyl protecting group in N-2-(t-butyloxycarbonyl)benzoylecgonine hydrazide with anhydrous HCl yields benzoylecgonine hydrazide hydrochloride. NMR and high resolution mass spectral analyses demonstrate that the benzoyl group of benzoylecgonine remains intact under the conditions of both carbodiimide coupling and anhydrous HCl treatment. By aldehyde-hydrazide condensation, the hydrazides are covalently conjugated to the carbohydrate residues of horseradish peroxidase (HRP). Dot blot analysis of the conjugates employing antibodies specific to benzoylecgonine demonstrates the presence of bound benzoylecgonine in HRP. The stoichiometry of benzoylecgonine residues to HRP may be determined by matrix-assisted laser desorption/ionization mass spectrometry (MALDI-MS). Mono-(N-2'-benzoylecgoninoyl)adipic dihydrazide gives a 2.5 to 3-fold higher coupling compared with benzoylecgonine hydrazide. Conjugates may also be prepared by the coupling of the carbodiimide activated benzoylecgonine to HRP that was derivatized with adipic dihydrazide.

Benzoylecgonine conjugates prepared according to this invention may be routinely used in cocaine detection methodology. The procedures described herein will be valuable to other investigators and for commercial companies for the preparation of benzoylecgonine conjugates of required stoichiometry and for the development of specific and sensitive immunological assays for cocaine detection.

For example, the benzoylecgonine conjugates of the present invention may be utilized in various immunoassays and diagnostic procedures such as those disclosed in U.S. Pat. Nos. 5,233,042 to Beuchler, 5,066,789 to Srinivasan et al., 5,369,007 to Kidwell, 4,197,237 to Lute et al, 5,376,667 to Somers et al. and 3,917,582 to Soffer et al, the entire subject matter of which is hereby incorporated herein by reference.

EXPERIMENTAL EXAMPLE

The following processes were utilized to synthesize benzoylecgonine hydrazide derivatives and benzoylecgonine HRP conjugates of the present invention.

1-Hydroxybenzotriazole (HBT), 1-ethyl-3-[3-(dimethylamino)-propyl]carbodiimide hydrochloride (EDC), adipic dihydrazide, t-butyl carbazate (N-2-t-butyloxycarbonyl hydrazide), dimethylacetamide, dimethyl sulfoxide, N-hydroxysuccinimide (NHS), dicyclohexyl carbodiimide (DCC), sinapinic acid, and silica gel thin-layer plates were purchased from Aldrich Chemical Co. (Milwaukee, Wis.). Biotin hydrazide and 6-biotinamido hexanoic hydrazide (Biotin-LC hydrazide) were obtained from Pierce Chemical Co. (Milwaukee, Wis.). HRP (type VI), 4-chloro-1-naphthol, 4-morpholineethane sulfonic acid (MES) and bovine serum albumin (BSA) were obtained from Sigma Chemical Co. (St. Louis, Mo.). Protein A-purified murine monoclonal antibody (PO1-99-11 M-P, 3.39 mg/ml) and a rabbit polyclonal antibody (PO1-99-13R-1F, 3.61 mg/ml) that were raised against benzoylecgonine were purchased from Biostride Inc. (Palo Alto, Calif.). Polyvinylidene difluoride (PVDF) membranes were from Millipore (Bedford, Mass.).

Unless otherwise mentioned, drying and concentration of solutions were performed by rotary vacuum evaporation at 30° to 40° C. Compounds on thin-layer chromatograms were visualized by a hand-held UV lamp and/or by exposing to iodine vapor.

IR spectra of compounds in KBr pellets were recorded with a Nicolet 170SX FT-IR spectrometer (Nicolet Instrument Corp., Madison, Wis.) with an on-line 'H- or proton NMR microcomputer data station. 'H-NMR studies were performed with a 270 MHz Nicolet Model NT 270 spectrometer (Nicolet Instrument Corp., Madison, Wis.) coupled to a Tecmeg data system. The spectra were recorded at 24° C. using tetramethylsilane as the internal standard.

Positive ion mode fast atom bombardment mass spectrometry (FAB-MS) analysis was performed with a JEOL SX102 mass spectrometer (JEOL U.S.A., Inc., Peabody, Mass.) using 6 kev xenon atoms as the ionization source. Samples (1 µL of 1 mg/mL solutions in methanol or water) were mixed with 1 µL of Magic Bullet matrix (dithiothreitol:dithioerythritol, 5:1) on the probe tip. Spectra were acquired at a resolution of 3000 and calibrated against an external standard.

High resolution FAB-MS analysis was performed with a JEOL SX102 mass spectrometer as described above at a resolution of 10,000.

For carbohydrate analysis, untreated HRP (10 µg) and periodate-oxidized HRP (10 µg) were hydrolyzed with 400 µL of 2.5M trifluoroacetic acid at 100° C. for 5 hours. The hydrolysates were evaporated in a Speed-Vac and the residues were dissolved in water and analyzed for neutral sugars and hexosamines using a Dionex BioLC system with amperometric detection (Dionex, Sunnyvale, Calif.). Analysis was performed on a CarboPac PAl high-pH anion exchange column (4×250 mm) (Dionex, Sunnyvale, Calif.) at a flow rate of 0.8 mL/min using 20 mM sodium hydroxide.

The following process was used to synthesize benzoylecgonine. To a solution of cocaine hydrochloride (400 mg in 5 ml of ice-cold distilled water) was added 2M sodium hydroxide until the solution was slightly alkaline (pH about 8.0). The cocaine base that precipitated as a white solid mass was recovered by centrifugation at 5000 X g and washed two times with 3 mL of ice-cold water. The pellet was used either directly for the preparation of benzoylecgonine or was lyophilized and stored in a desiccator over solid sodium hydroxide.

The cocaine base (300 mg) was suspended in 10 ml of distilled water and heated under reflux in an oil bath at 90° C. for 18 h. The solution was then concentrated under reduced pressure to 1.5 mL and was then lyophilized. The product was crystallized from hot water and its m.p. determined. Benzoylecgonine was further characterized by IR, H-NMR and high resolution FAB-MS analyses.

The following process was utilized in preparing benzoylecgonine hydrazide hydrochloride. Benzoylecgonine (149 mg, 0.05 mmol), HBT (68 mg, 0.5 mmol) and t-butyl carbazate (66 mg, 0.5 mmol) were dissolved in dimethylacetamide (1.5 mL) and stirred to obtain a clear solution. EDC (97 mg, 0.5 mmol) was added. After stirring overnight at room temperature, water (1.5 mL) was added and the solution was extracted with ethyl acetate (5×2.5 mL). The combined extracts were washed successively with water (8 mL) and saturated saline (8 mL), and then dried over anhydrous magnesium sulfate. The solution was applied to a silica gel (60–200 mesh) column (0.7×15 cm) equilibrated with ethyl acetate:n-hexane (1:1, v/v) and washed with the same solvent (150 ml). The bound N-2-(t-butyloxycarbonyl) benzoylecgonine hydrazide (identified by mass spectral analysis) was eluted with chloroform:methanol (9:1, v/v) and the elution was monitored by TLC using the same solvent. Fractions containing N-2-(t-butyloxycarbonyl) benzoylecgonine hydrazide were combined and evaporated with a yield of 90 mg. The compound was characterized by H-NMR (in $CDCl_3$:$CD_3OH$, 9:1 v/v) and high resolution FAB-MS analyses.

The N-2-(t-butyloxycarbonyl)benzoylecgonine hydrazide (90 mg) was dissolved in dry ethyl acetate (0.5 mL) and cooled in an ice-bath. To the solution was added cold ethyl acetate (2 mL) saturated with anhydrous HCl. After 30 minutes at room temperature, excess HCl was removed by passing a jet of nitrogen gas through the solution. The resulting benzoylecgonine hydrazide hydrochloride was precipitated with anhydrous ethyl ether, collected by centrifugation, dried in a vacuum desiccator and then characterized by high resolution FAB-MS.

The following process was utilized in synthesizing mono-(N-2'-benzoylecgoninoyl)adipic dihydrazide. Benzoylecgonine (100 mg, 0.34 mmol), HBT (45 mg, 0.34 mmol) and adipic dihydrazide (232 mg, 1.32 mmol) were suspended in a mixture of dimethylacetamide (5 mL) and dimethyl sulfoxide (5 mL). The mixture was stirred for 30 minutes at room temperature. To the cloudy solution, EDC (97 mg, 0.5 mmol) was added and the mixture stirred overnight at room temperature. Water (20 mL) was added and the solution was extracted with ethyl acetate (5×20 mL). The aqueous phase was then deionized with AG 4×4 (free base) ion exchange resin and lyophilized. The solid was dispersed in ethanol and stirred for 2 hours to obtain a fine suspension and centrifuged. The precipitate contained unreacted adipic dihydrazide and was discarded. The ethanol solution was chromatographed on a silica gel column (1×15 cm) using ethanol:water (85:15, v/v). Fractions (2 mL) were collected and analyzed by TLC using the above solvent. Mass spectral analysis demonstrated that the desired compound, mono-(N-2'-benzoylecgoninoyl)adipic dihydrazide, was eluted in fractions 10 through 25 along with significant amounts of other compounds. The product, mono-(N-2'-benzoylecgoninoyl) adipic dihydrazide ($R_f$ value relative to adipic dihydrazide=0.27) was purified (yield, 49 mg) by preparative TLC using ethanol:water (85:15, v/v) and characterized by high resolution FAB-MS.

The following process was utilized for conjugation of benzoylecgonine hydrazides to HRP. To a solution of HRP (2.4 mg) in 50 mM sodium acetate (2.16 mL), pH 5.0 at 4° C., was added 100 mM sodium metaperiodate in 50 mM sodium acetate (0.24 mL), pH 5.0. The solution was allowed to stand at 4° C. for 30 minutes in the dark, dialyzed against 50 mM sodium acetate, pH 5.0 (24 hours, several changes) and then concentrated to 0.6 mL using a Centricon-10 centrifugal microconcentrator (Amicon, Danvers, Mass.). Benzoylecgonine hydrazide hydrochloride (3.8 mg in 100 µL of water, 200-fold molar excess) was added and allowed to react at room temperature for 4 hours. The solution was then dialyzed against 50 mM sodium phosphate, pH 7.2. Mono-(N-2'-benzoylecgoninoyl) adipic dihydrazide, biotin hydrazide and biotin-LC hydrazide were conjugated similarly to the carbohydrate residues of HRP.

The following process was utilized for direct conjugation of benzoylecgonine to adipic dihydrazide-derivatized HRP. HRP (2 mg) was oxidized with periodate as described above and dialyzed against 50 mM sodium acetate, pH 5.0. The solution was concentrated (final volume 1 mL) using a Centricon-10 microconcentrator, treated with adipic dihydrazide (1.8 mg in 100 µL of 50 mM sodium acetate, pH 5.0) and allowed to react at room temperature for 4 hours. The solution was dialyzed against 100 mM MES acid, pH 4.7 and then concentrated to 400 µL using a Centricon-10 microconcentrator. In a separate test tube, EDC (5.0 mg in 100 µL of 100 mM MES, pH 4.7) was added to a solution of benzoylecgonine (2.5 mg in 100 µL of 100 mM MES, pH 4.7) and allowed to react at room temperature. After 10–15 minutes, adipic dihydrazide-modified HRP was added to EDC-activated benzoylecgonine and allowed to react at room temperature. Aliquots (200 µL) of this solution drawn at 30 minutes, 1 hour and 2 hours were dialyzed extensively against 20 mM sodium phosphate, pH 7.4, and analyzed by MALDI-MS.

The following process was utilized for dot blot analysis of benzoylecgonine-HRP conjugates. The benzoylecgonine residues covalently bound to HRP were identified by dot blot analysis using mAb and a polyclonal antibody that are specific to benzoylecgonine. The benzoylecgonine antibodies (amounts ranging from 4 µg to 0.03 µg per spot) were spotted on PVDF membranes using a dot blot apparatus. The membranes were either stained with Amido black to visualize the amounts of applied antibody (data not shown) or blocked with a 1% solution of BSA in 10 mM Tris-HCl, 150 mM NaCl, pH 8.0 at room temperature for 2 hours. The blocked membranes were treated with BE-HRP (4 µg/ml) in 50 mM Tris-HCl, 150 mM NaCl, pH 8.0 containing 0.05% Tween 20 at room temperature for 1 hour. The membranes were washed 3–4 times with 50 mM Tris-HCl, 150 mM NaCl, pH 8.0 containing 0.05% Tween 20 to remove unbound BE-HRP and then treated with 4-chloro-1-naphthol reagent. After 5–10 minutes of color development, the membranes were washed with excess distilled water.

The following process was used for mass spectrometry analysis of benzoylecgonine-HRP and biotin-HRP conjugates. MALDI-MS of the conjugates was performed using a Kratos MALDI III mass spectrometer (Shimadzu Scientific Instruments, Columbia, Md.) operated in a linear mode at an accelerating voltage of 22 kev with detection of positive ions. Conjugates (5–10 µM in 0.5 µL of water) were placed on the sample slide and sinapinic acid (0.8 µl of 10 mg/mL solution in 50% aqueous acetonitrile, 0.05% trifluoroacetic acid) was added. The slide was then dried in a vacuum desiccator for 10 minutes. Desorption/ionization was accomplished by a nitrogen UV laser (337 nm). 100 scans were accumulated over a 2 mm stripe across the sample spot. The instrument was calibrated against BSA as an external standard ($(M+H)^+$=66431 and $(M+2H)^{2+}$=33216).

The following process was utilized for the analysis of benzoylecgonine. Benzoylecgonine was prepared by heating aqueous solution of cocaine base under optimal reaction conditions to obtain quantitative conversion without any degradation. FAB-MS analysis showed that the $(M+H)^+$ ion of cocaine (304 amu) completely disappeared while a new $(M+H)^+$ ion of benzoylecgonine (290 amu) appeared. The quantitative conversion of cocaine to benzoylecgonine was further demonstrated by IR and NMR analyses. Benzoylecgonine showed IR absorption peaks at 1631 cm$^{-1}$ (carboxylic group), 1724 cm$^{-1}$ (aryl ester carbonyl) and 3450 cm$^{-1}$ (broad, carboxylic —OH), whereas cocaine gave absorption peaks at 1737 cm$^{-1}$ (methyl ester carbonyl) and 1710 cm$^{-1}$ (aryl ester carbonyl). The 'H-NMR (or proton-NMR) (in CDCl$_3$) of benzoylecgonine contained resonance signals at δ8.20–7.31 (5H, m, —C$_6$H$_5$) and 2.58–2.44 (3H, s, —NCH$_3$); the methyl ester resonance at δ3.85–3.66 (3H, s, —COOCH$_3$) that was observed for cocaine was absent. Upon recrystallization from hot water, benzoylecgonine was obtained as white needles with a m.p. of 88°–90° C. (lit. 86°–92° C.). High resolution mass spectral analysis of the purified product gave $(M+H)^+$ ion at 290.1388 (calc. 290.1392, C$_{16}$H$_{20}$NO$_4$).

The following process was utilized for analysis of benzoylecgonine hydrazide. To accomplish a facile conjugation of benzoylecgonine to HRP by aldehyde-hydrazide condensation reaction, two hydrazide derivatives of benzoylecgonine were synthesized and characterized. The carbodiimide-activated benzoylecgonine was reacted with t-butyloxycarbonyl hydrazide using HBT as a catalyst to obtain N-2-t-butyloxycarbonylbenzoylecgonine hydrazide (FIG. 1) in 58% yield. The product was purified on a silica gel column and characterized by NMR and FAB-MS. 'H-NMR (or proton NMR) analysis showed resonance signals at δ9.32–8.27 (2H, b, —CONH—NHCO—O—t—Bu), 1.76–106 (9H, s, —O—C(CH$_3$)$_3$) and 8.24–7.06 (5H, m, —CO—C6H$_5$). These results demonstrated that the benzoyl ester moiety remained intact under the reaction conditions employed for hydrazide formation. High resolution FAB-MS analysis gave $(M+H)^+$ ion at 404.2169 (calc. 404.2185, C$_{21}$H$_{30}$N$_3$O$_5$).

The protective t-butyloxy group in N-2-(t-butyloxycarbonyl)benzoylecgonine hydrazide was removed with anhydrous HCl and the product, benzoylecgonine hydrazide hydrochloride, was obtained in almost quantitative yield. High resolution FAB-MS analysis gave $(M+H)^+$ at 304.1622 (calc. 304.1661, C$_{16}$H$_{22}$N$_3$O$_3$). The following process was utilized for analysis of mono-(N-2'-benzoylecgoninoyl)adipic dihydrazide. The observed coupling efficiency of benzoylecgonine to periodate-oxidized HRP was much lower than that expected considering the number of available aldehyde groups (see below) and the ease of aldehyde-hydrazide condensation. This is presumably due to steric hindrance from the bulky benzoyl group on the adjacent carbon atom. To overcome this disadvantage, an adipic acid spacer arm-containing hydrazide was synthesized. Carbodiimide-activated benzoylecgonine was condensed with adipic dihydrazide using HBT as a catalyst. The product, mono-(N-2'-benzoylecgoninoyl)adipic dihydrazide, was obtained in about 32% yield after purification by ethanol precipitation to remove unreacted adipic dihydrazide followed by silica gel chromatography and preparative TLC. FAB-MS showed $(M+H)^+$ and $(M+Na)^+$ ions at 446 amu and 468 amu, respectively. High resolution mass spectral analysis gave $(M+H)^+$ at 446.2381 (calc. 446.2403, $C_{22}H_{32}N_5O_5$).

Figure 2:
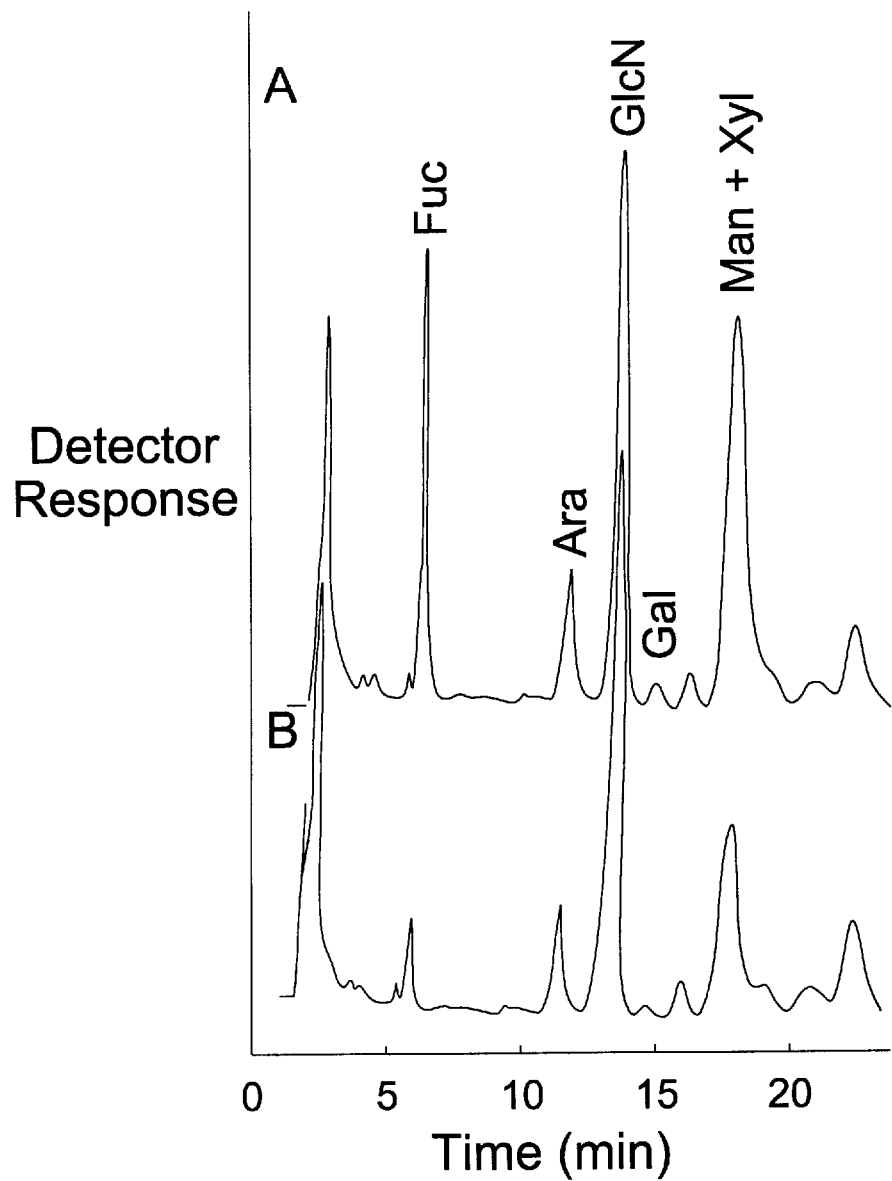
FIG. 2 demonstrates a carbohydrate compositional analysis of HRP (panel A) and periodate-oxidized HRP (panel B). HRP (10 μg) and periodate-oxidized HRP (10 μg) were hydrolyzed as described herein. The hydrolysates corresponding to 2 μg protein were chromatographed on a CarboPac PA1 high-pH anion exchange column (4×250 mm). The elution was with 20 mM sodium hydroxide at a flow rate of 0.8 mL/min. Sugars were identified by comparing their retention times with those of standards. Fuc represents fucose; Ara represents arabinose (possibly from a polysaccharide contaminant in the HRP preparation); GlcN represents glucosamine (derived from N-acetylglucosamine); Gal represents galactose; Man represents mannose; Xyl represents xylose.

The following process was used for analysis of the conjugation of benzoylecgonine hydrazides to the carbohydrate moieties of HRP. HRP contains 8 N-linked oligosaccharides with $Xyl(Man)_2Man(Fuc)GlcNAc_2$— structures. The fucose, xylose, and two out of three mannose residues of each HRP oligosaccharide structure are amenable to periodate oxidation. In all, there are approximately 32 unsubstituted terminal sugar residues that can potentially be oxidized by periodate. Generally, periodate oxidation of glycoproteins to generate aldehyde groups on terminal hexoses are performed using 10 to 20 mM periodate for 30 to 40 minutes in the dark. In the present invention, HRP was oxidized with periodate under relatively mild conditions to generate aldehyde groups on the terminal sugar residues. The carbohydrate compositional analysis of the periodate-oxidized HRP demonstrated that approximately 80% of fucose, and about 50% of combined mannose and xylose (FIG. 2) were oxidized. From this result, it is estimated that about 18 sugar residues of HRP were oxidized.

Figure 3A:
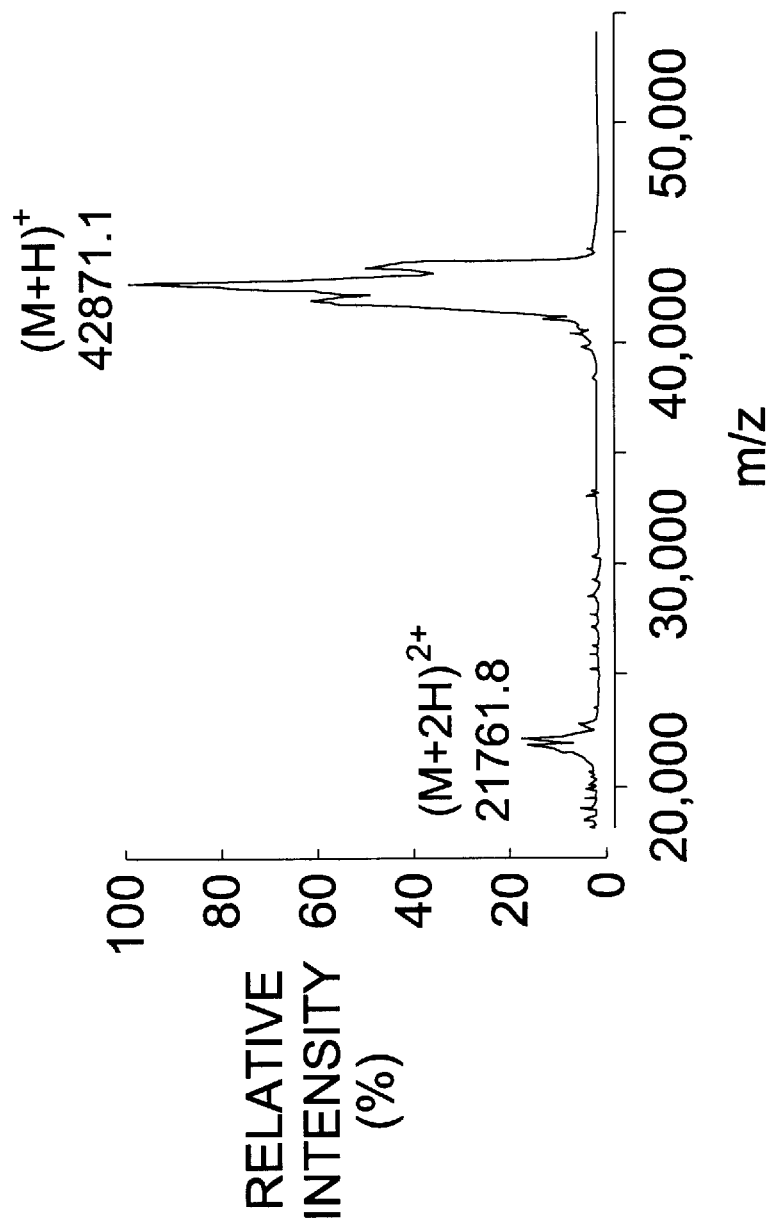
FIG. 3 represents a mass spectral analysis of HRP and BE-HRP conjugates. Shown are the positive ion mass spectra obtained by the matrix-assisted laser desorption/ionization and time-of flight mass analysis of HRP (panel A), benzoylecgonine hydrazide-HRP conjugates (panel B), and mono-(N-2'-benzoylecgoninoyl)adipic hydrazide-HRP conjugates (panel C). The measured molecular weights for $(M+H)^+$ and $(M+2H)^{2+}$ ions are indicated.
Figure 3B:
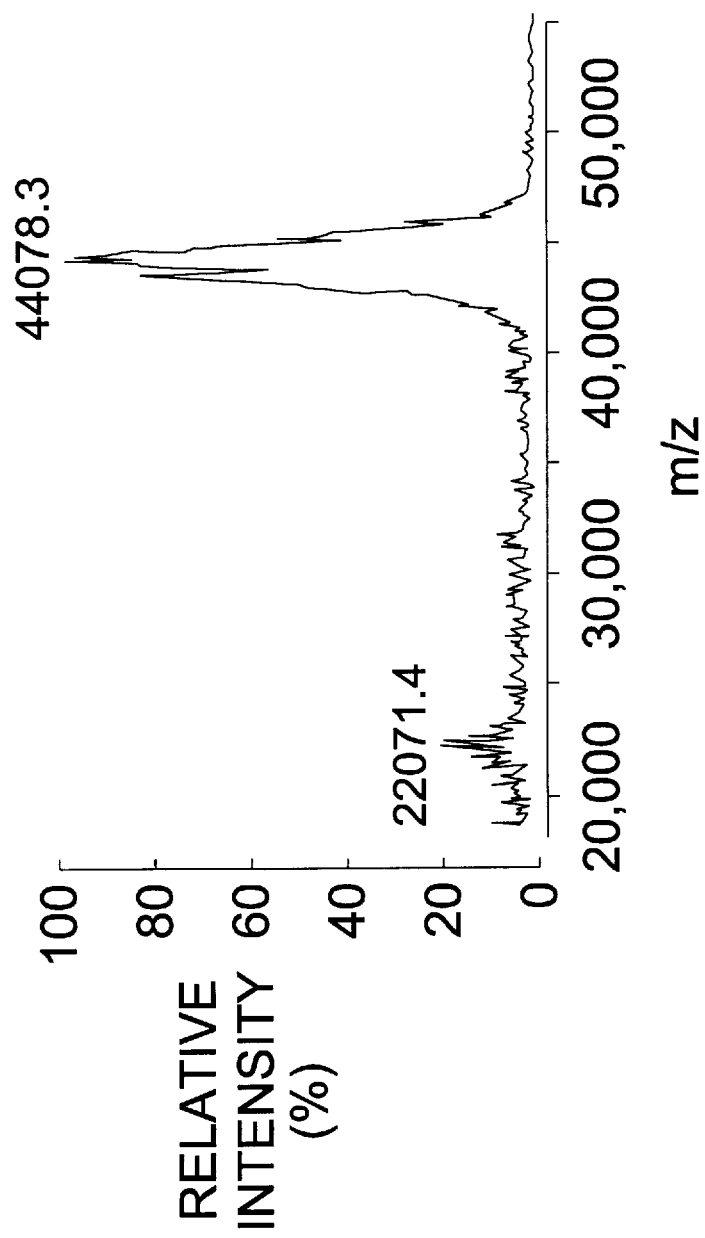
Figure 3C:
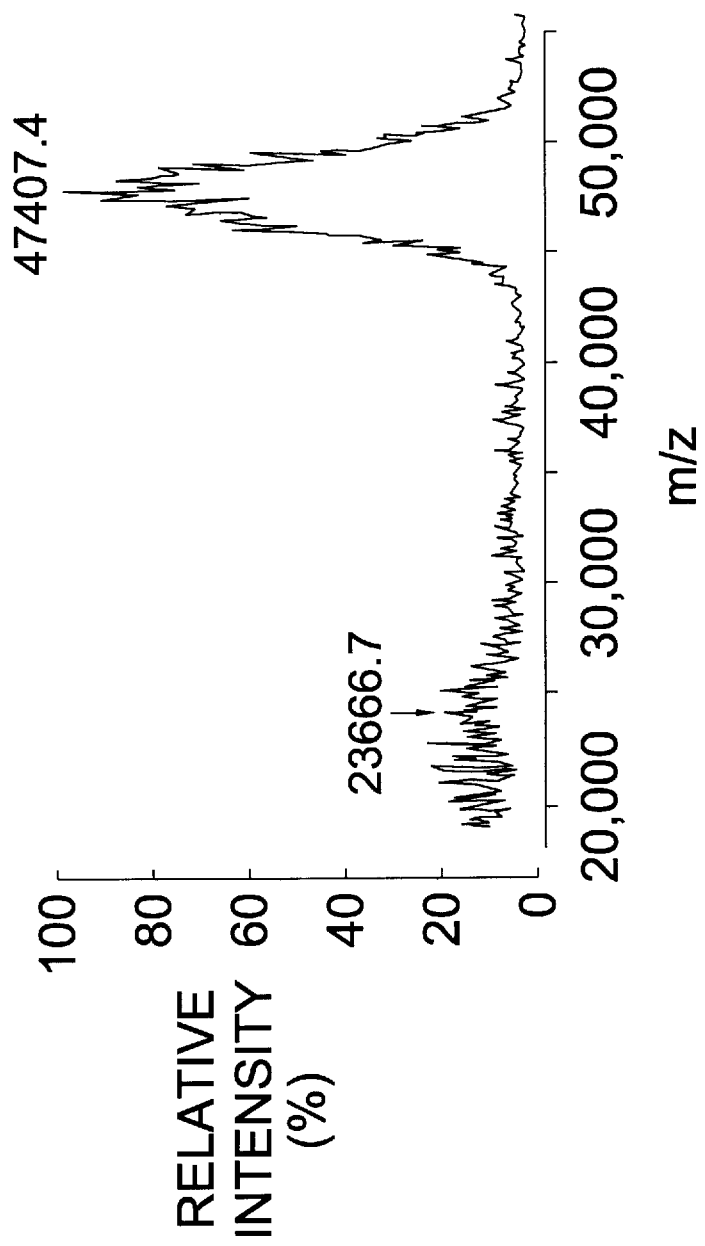

On average only 4 moles of benzoylecgonine hydrazide were coupled to 1 mole of HRP even though a 100 to 200-fold (10–150-fold can also be used) molar excess of the hydrazide was used. MALDI-MS analysis showed that the molecular weight of HRP was increased by 989 and 1207 (respectively, 3.5 and 4.2 moles of benzoylecgonine per mole of HRP) in two different preparations of BE-HRP (FIG. 3, panel B and data not shown). Considering that as many as 36 aldehyde groups were generated on periodate oxidation of HRP (see above) and that the hydrazide-aldehyde additions are facile, the low efficiency of conjugation of benzoylecgonine hydrazide to HRP is likely due to the steric hindrance caused by the neighboring bulky benzoyl moiety. Supporting this conclusion, the DCC-activated benzoylecgonine failed to form a succinimidyl ester with NHS even after a prolonged reaction. However, FAB-MS of the reaction mixture indicated that a stable benzoylecgonine-DCC adduct was formed $((M+H)^+=496)$.

The amount of mono-(N-2'-benzoylecgoninoyl)adipic dihydrazide that coupled to periodate-oxidized HRP was 2.5 to 3-fold higher compared with benzoylecgonine hydrazide. MALDI-MS analysis demonstrated that, after conjugation of mono-(N-2'benzoylecgoninoyl)adipic dihydrazide, the molecular weight of HRP increased by 4536 (10.6 moles of benzoylecgonine residues per mole of HRP) in one of the BE-HRP preparations (FIG. 3, panel C). This result, taken together with those described above, suggests that the steric hindrance caused by the benzoyl group can be considerably minimized by introducing a spacer arm and, thus, more benzoylecgonine residues may be coupled to HRP.

The coupling of two commercially available hydrazides, biotin hydrazide and biotin-LC hydrazide, to periodate-oxidized HRP was studied to determine whether the length of the spacer arm is critical for efficient conjugation. It was concluded that any difference in coupling efficiency between these two compounds must be related to the steric effect exerted by the bulky fused ring system. The molecular weight of HRP was shifted by 1559 and 2885 after conjugation with biotin hydrazide and biotin-LC hydrazide respectively, as demonstrated by MALDI-MS analysis (data not shown). These molecular weight shifts correspond to coupling of 6.5 moles of biotin hydrazide and 8.2 moles of biotin-LC hydrazide to HRP. The data suggest that the additional spacer arm in biotin-LC hydrazide has a significant contribution toward the coupling efficiency. From these data, it was inferred that a longer spacer arm, such as the one used in this invention, optimizes coupling of benzoylecgonine to periodate-oxidized HRP.

The following process was utilized in the conjugation of benzoylecgonine to adipic dihydrazide-derivatized HRP. This method involves in situ conjugation of EDC-activated benzoylecgonine to adipic dihydrazide-derivatized HRP was also conducted. In this approach, periodate oxidized-HRP was first reacted with adipic dihydrazide. MALDI-MS analysis of the product revealed that as many as 15–17 adipic dihydrazide molecules (approximately 2 residues per oligosaccharide chain of HRP) were coupled to 1 mole of HRP (data not shown). The coupling did not increase with further increase in reaction time, suggesting that each oligosaccharide chain of HRP can accommodate no more than two adipic dihydrazide residues, even though considerably more aldehyde groups are available (see above). The resultant adipic dihydrazide-derivatized HRP was then allowed to react with the carbodiimide-activated benzoylecgonine. MALDI-MS analysis of the reaction mixture at different time intervals indicated that the coupling of benzoylecgonine residues to HRP was essentially complete within 30 minutes. Approximately 2.5 to 3 moles of benzoylecgonine were coupled to 1 mole of HRP (data not shown). The primary amine groups of the adipic dihydrazide side chain in the derivatized HRP are not protonated at pH 4.7 ($pK_a$ of a hydrazide is about 2.6) and, thus, they are expected to react preferentially with carbodiimide-activated benzoylecgonine. On the other hand, the lysine side chain and amino terminal primary amino groups of HRP are highly protonated and, consequently, they should not form amide bonds with benzoylecgonine. Therefore, it is likely that the coupling of carbodiimide-activated benzoylecgonine to adipic dihydrazide-derivatized HRP is to the carbohydrate-linked hydrazide groups, rather than directly to the polypeptide.

Figure 4:
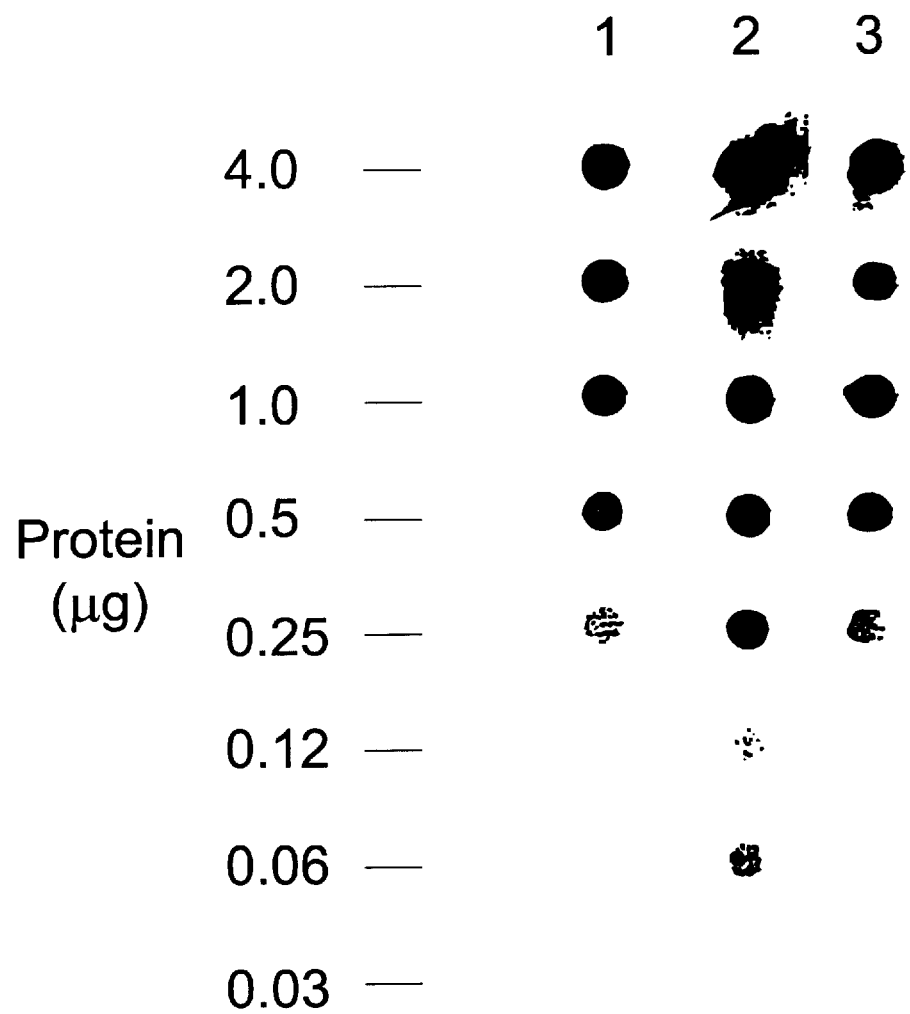
FIG. 4 demonstrates dot blot analysis of benzoylecgonine-HRP conjugates. The indicated amounts of the benzoylecgonine monoclonal antibody were spotted onto PVDF membranes. After blocking with 1% BSA, the membranes were blotted with BE-HRP conjugates and then visualized with 4-chloro-1-naphthol reagent as described herein. Lane 1 represents a benzoylecgonine hydrazide-HRP conjugate, lane 2 represents a mono-(N-2'-benzoylecgoninoyl)adipic dihydrazide-HRP conjugate, and lane 3 represents a benzoylecgonine-adipic dihydrazide-derivatized HRP conjugate.
Figure 5:
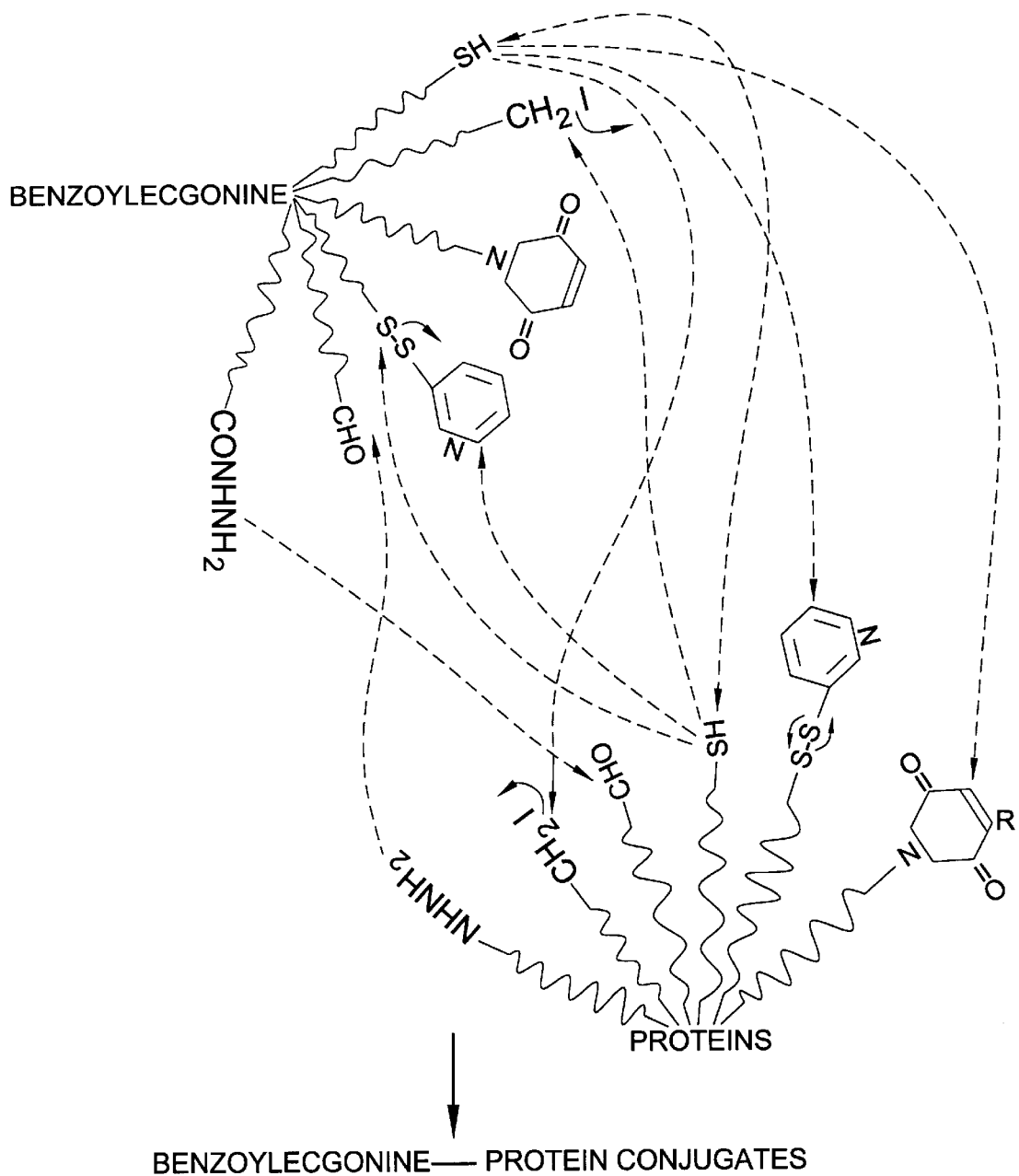
FIG. 5 illustrates a schematic diagram for the crosslinking of benzoylecgonine derivatives to proteins.
Figure 6:
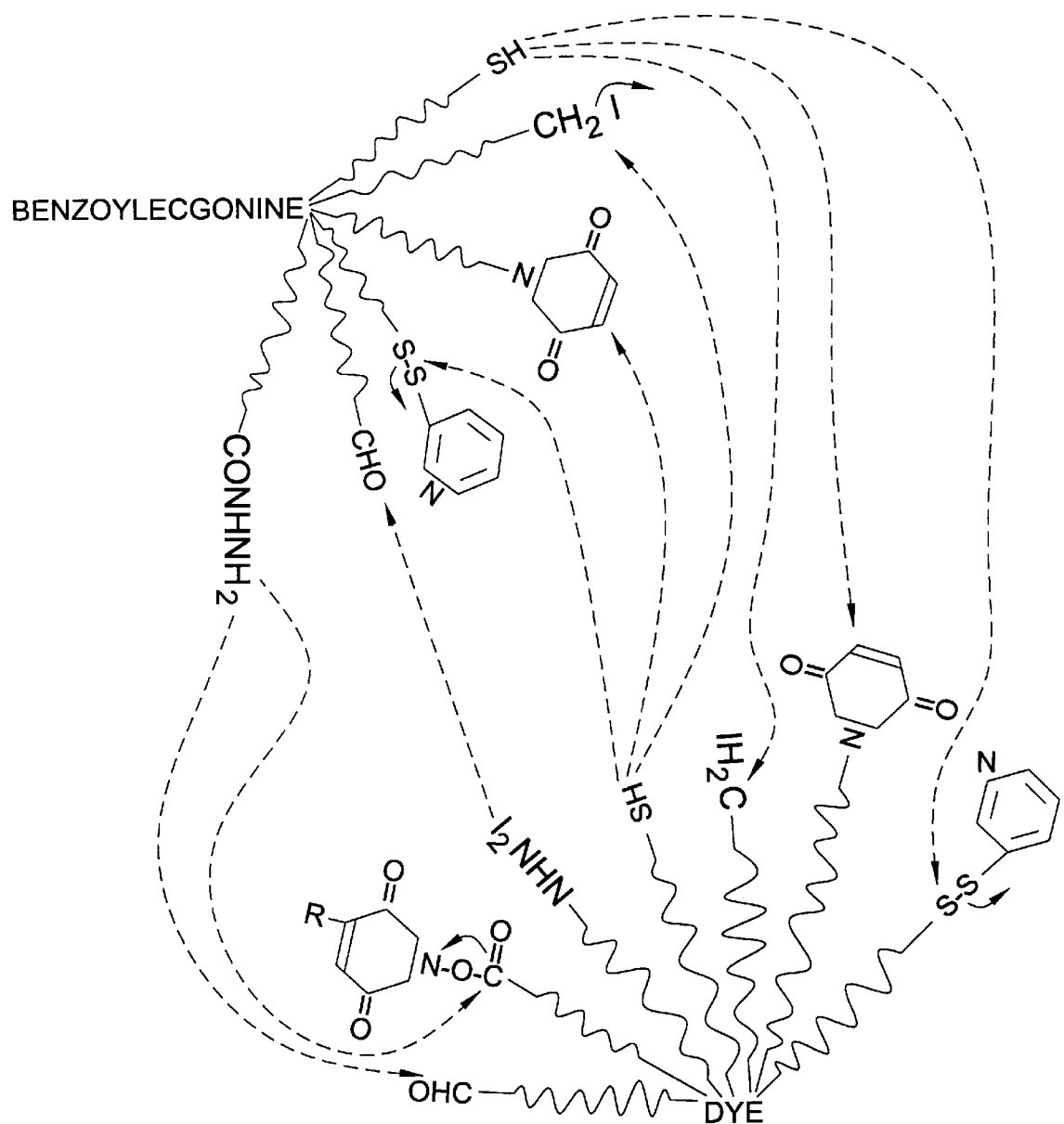
FIG. 6 illustrates a schematic diagram for the crosslinking of benzoylecgonine derivatives to dyes.

The following process was utilized in the analysis for the identification of benzoylecgonine residues bound to HRP. The BE-HRP conjugates were analyzed for their ability to bind a mouse mAb against benzoylecgonine (FIG. 4). The HRP conjugates of the benzoylecgonine hydrazides and those prepared by coupling benzoylecgonine to the adipic dihydrazide-modified HRP were able to detect as little as 30–60 ng of the mAb. Similar results were obtained by dot blot analysis using a polyclonal rabbit anti-benzoylecgonine IgG (data not shown). These results demonstrate that benzoylecgonine is covalently coupled to HRP and that the HRP activity is retained.

A variety of other functional groups can be introduced to the two hydrazide derivatives of benzoylecgonine so that these can be cross-linked (conjugated) to proteins, biotins or dyes. These benzoylecgonine cross-linked (conjugated) proteins or dyes are useful for diagnostic applications.

EXAMPLES 1–4

These examples set forth benzoylecgonine hydrazide derivatives containing easy leaving groups such as halogen.

Example 1

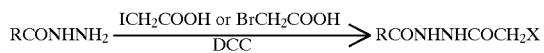

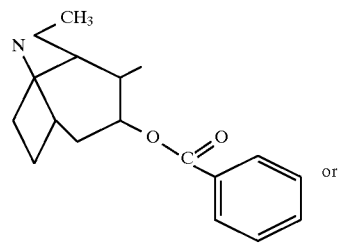
or

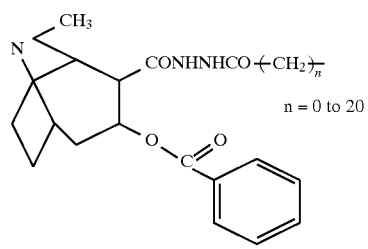
n = 0 to 20 wherein X is Cl, Br, or I.

Example 2

R—CONHNH₂ +

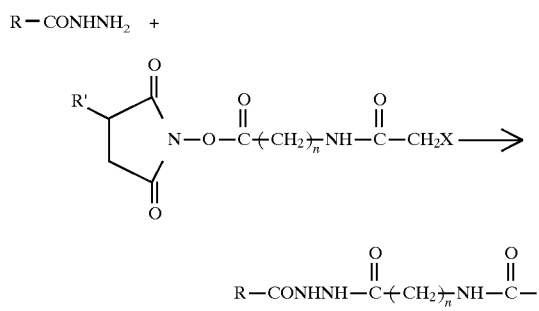

wherein
n is CL, Br, or I;
R' is NaSO₃⁻ or H; and
R and X are as above.

Example 3

RCONHNH₂ +

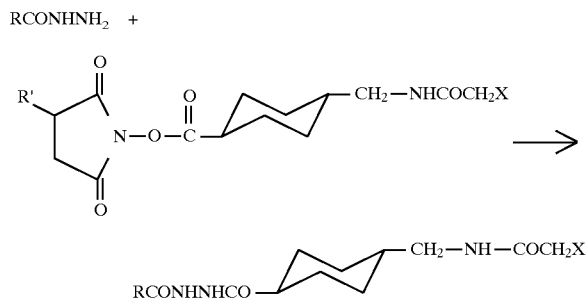

wherein R', X and R are as above.

Example 4

RCONHNH₂ +

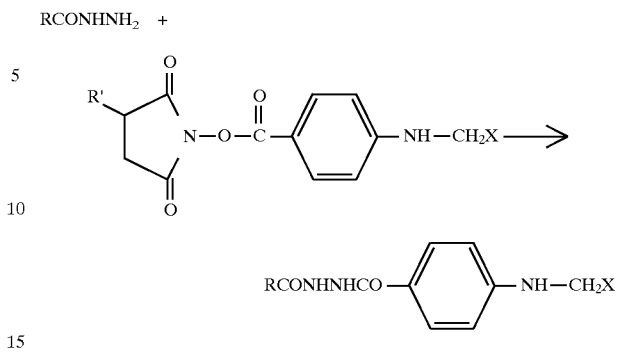

wherein R', R and X are as above.

Examples 5–8

The following examples set forth benzoylecgonine hydrazide derivatives containing SH or protected SH groups.

Example 5

RCONHNH₂ +

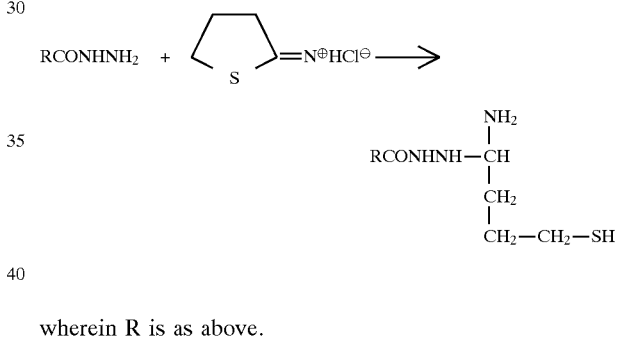

wherein R is as above.

Example 6

RCONHNH₂ +

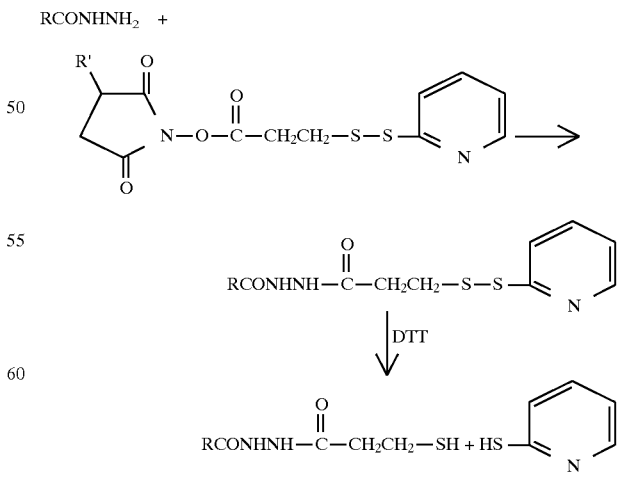

wherein R' and R are as above.

Example 7

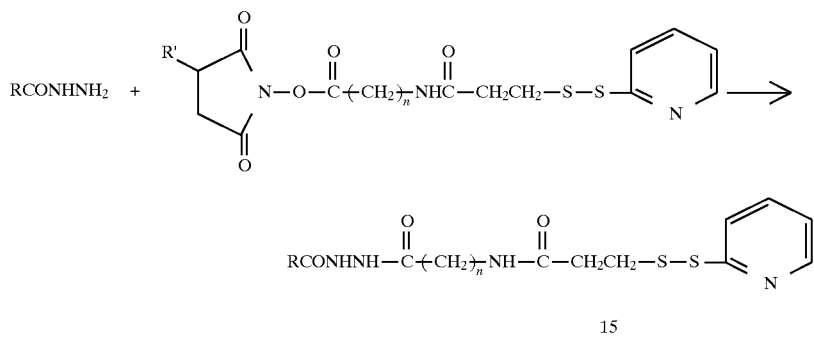

wherein R, R' and n are as above.

Example 8

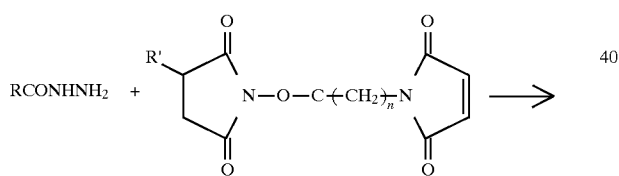

wherein R is as above.

Examples 9–12

The following examples set forth benzoylecgonine hydrazide derivatives containing electrophilic centers.

Example 9

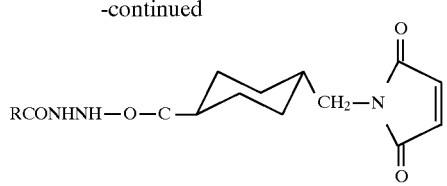

wherein R, R' and n are as above.

Example 10

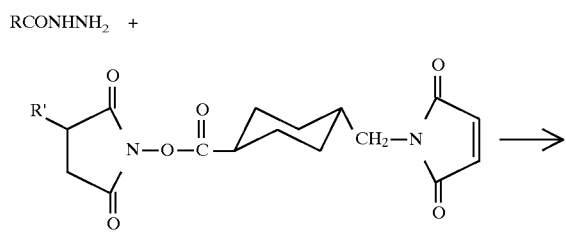

-continued

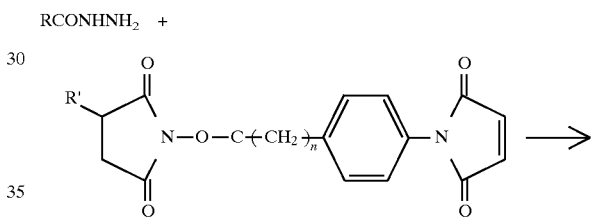

where R and R' are as above.

Example 11

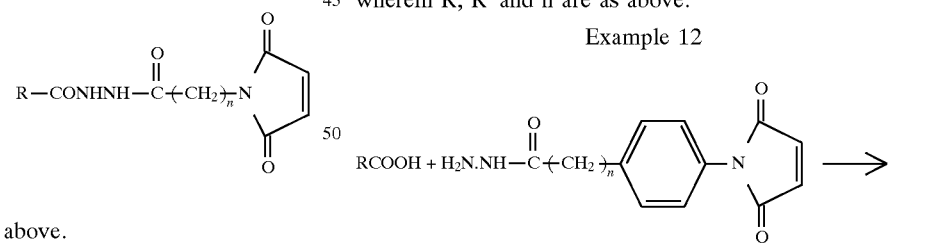

wherein R, R' and n are as above.

Example 12

RCOOH + H$_2$N.NH—C(—CH$_2$—)$_n$—[4-maleimidophenyl] →

RCONH—NH—C(—CH$_2$—)$_n$—[4-maleimidophenyl]

wherein R and n are as above.

Examples 13–16

The following examples set forth benzoylecgonine hydrazide derivatives containing aldehyde groups.

Example 13

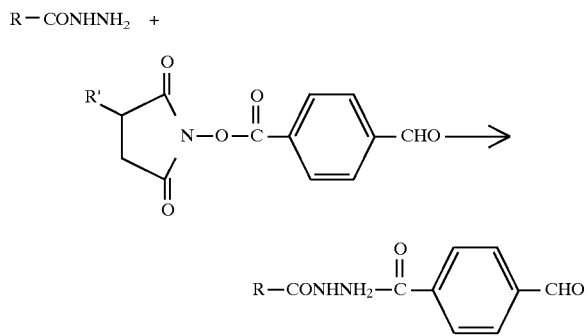

wherein R and R' are as above.

Example 14

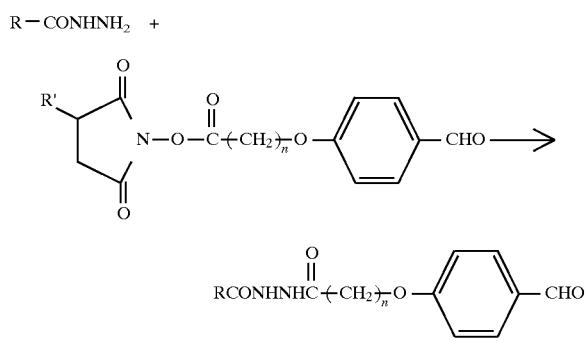

wherein R, R' and n are as above.

Example 15

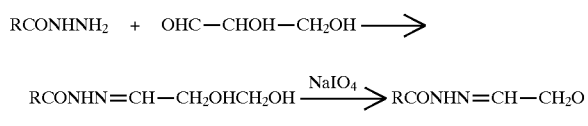

Example 16

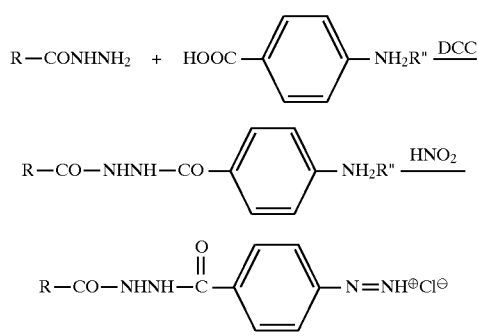

wherein R is as above and R" is $H_2$ trityl group or related protecting groups.

Examples 17–18

The following examples set forth direct derivatization of benzoylecgonine using the same chemistry as that was used for hydrazides preparation.

Example 17

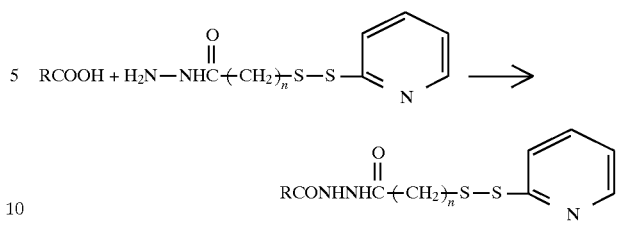

wherein R and n are as above.

Example 18

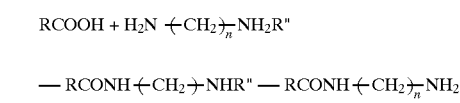

wherein
  R and n are as above; and
  R" is H, a Trityl group or related protecting groups.

Examples 19–24

The following examples set forth derivatization of proteins for benzoylecgonine cross-linking. Such proteins include, for Example, Keyhole Limpet Hemocyanin (KLH), Bovine Serum Albimum (BSA), Horseradish Peroxidase (HRP), Alkaline Phosphatase (AP), antibodies, enzymes, glycoproteins, polysaccharides, filter paper or the like.

Example 19

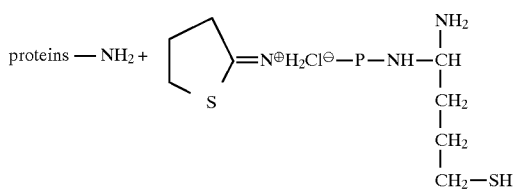

wherein P is KLH, BSA, HRP, AP, antibody, glycoprotein, filter paper, polysaccharide, etc.

Example 20

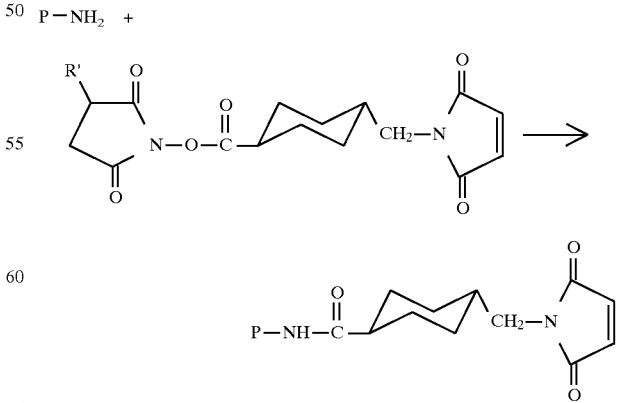

wherein P, R' are as above.

Example 21

[Structure: P—NH₂ + succinimidyl ester with R' group, —O—C(=O)—(CH₂)ₙ— linked to phenyl-maleimide]

→ —P—NH—C(=O)—(CH₂)ₙ—phenyl—maleimide wherein P, R' and n are as above.

Example 22

[Structure: P—NH₂ + succinimidyl ester with R' group, N—O—C(=O)—(CH₂)ₙ—N-maleimide]

→ P—NH—C(=O)—(CH₂)ₙ—N-maleimide wherein P, R' and n are as above.

Example 23

[Structure: P—NH₂ + succinimidyl ester, N—O—C(=O)—(CH₂)ₙ—NH—C(=O)—CH₂I]

→ P—NH—C(=O)—(CH₂)ₙ—NH—C(=O)—CH₂I wherein P and R' are as above.

Example 24

P—NH₂ +

[Structure: succinimidyl ester with R', N—O—C(=O)—CH₂—CH₂—S—S—pyridyl]

→

PNH—C(=O)—CH₂CH₂—S—S—pyridyl wherein P and R' are as above.

Examples 25–27

The following examples set forth conjugation of benzoylecgonine to dyes.

Example 25

R—CONHNH₂ + HOOC-Dye $\xrightarrow{DCC}$ RCONHNHCO-Dye conjugate wherein R is the same as above.

Example 26

RCOOH + H₂N-Dye $\xrightarrow{DCC}$ RCONH-Dye conjugate wherein R is the same as above.

Example 27

RCONHNH₂ + [succinimidyl ester with R', N—O—C(=O)—(CH₂)ₙ—NH—C—Dye] →

RCONHNH—C(=O)—(CH₂)ₙ—NH—C—Dye wherein R and R' are the same as above.

Examples 28–30

The following examples set forth conjugation of benzoylecgonine to biotins.

Example 28

R—CONHNH₂ + HOOC~Biotin → RCONHNHCO—Biotin wherein R is as above.

Example 29

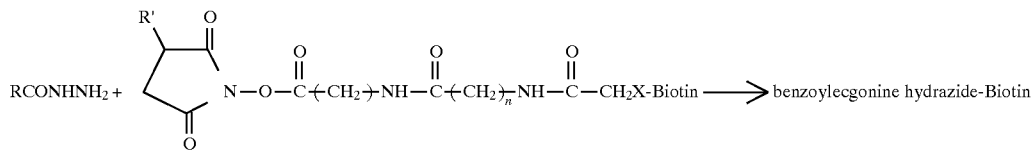

wherein X, R and R' are as above.

Example 30

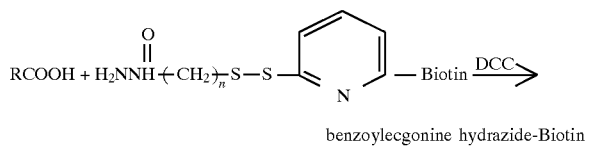

where R and n are as above.

What is claimed is:

1. A hydrazide derivative of benzoylecgonine represented by the following formula:

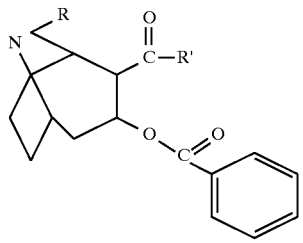

wherein,

R is H or $CH_3$;

R' is $-NH-NH_2$, $(NH)_2CO(CH_2)_nCONHNH-$ and n is an integer of 0 to 20.

2. A hydrazide derivative according to claim 1, wherein n is an integer from 1 to 10.

3. A hydrazide derivative according to claim 1, wherein n is an integer from 1 to 5.

4. A hydrazide derivative according to claim 1 selected from the group consisting of benzoylecgonine hydrazide and mono-(N-2'-benzoylecgoninoyl)adipic dihydrazide.

* * * * *